Figure 1:
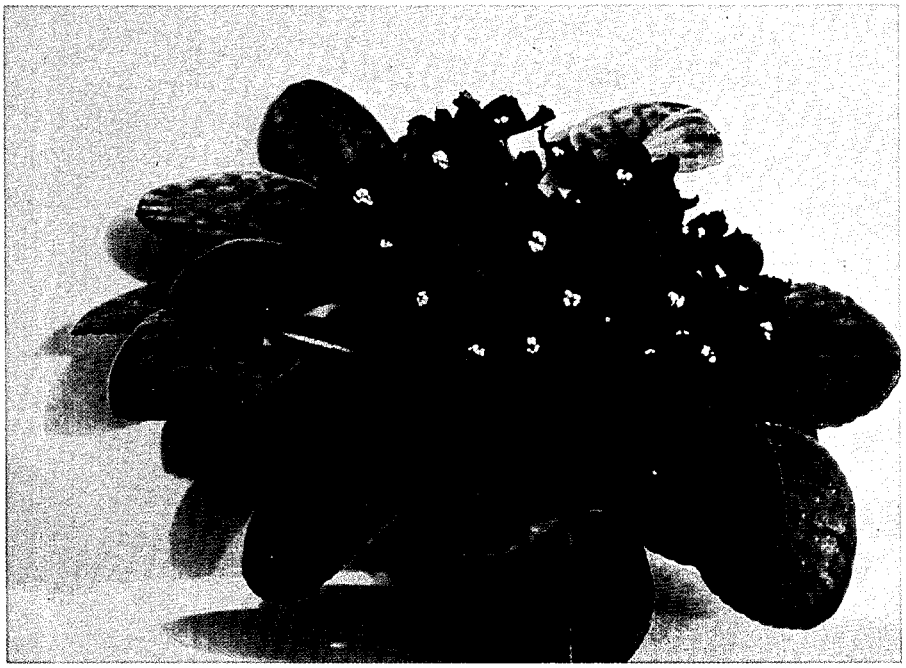

United States Patent [19]

Holtkamp

[11] Plant 4,189

[45] Jan. 17, 1978

[54] AFRICAN VIOLET PLANT

[76] Inventor: Reinhold Holtkamp, Wertherstrasse 112, 4294 Isselburg, Germany

[21] Appl. No.: 746,223

[22] Filed: Nov. 30, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

This invention relates to a novel african violet plant which bears relatively large, unfading violet-blue blossoms over a long period of time.

2 Drawing Figures

The present invention comprises a new and distinct cultivar of african violet plant, botanically known as *Saintpaulia ionantha,* and hereinafter referred to by the cultivar name New York.

New York, referred to during the selection process by the designation (b 213/3) 34/76 is a product of a planned breeding program which had the objective of creating a new african violet plant combining certain of the desired characteristics of the parent cultivars. The female, or seed parent is unpatented and designated SL blue (color 1-13) and was selected for breeding due to its single flower shape and blue color form, rich flowering, medium green and attractive leaves and its upright flower stems. The male, or pollen parent is also unpatented and is designated XX 224 blue star-shaped (color 1-13) and was selected due to its star-shaped, large flowers having intensive blue color and its tight anther formation, golden yellow in color, which provides a pleasing and attractive contrast to the blue flower color of the parent.

The cross was made by me in Isselburg, West Germany, and the new cultivar was selected as a flowering plant within the progeny of the stated cross by me in a controlled environment in Isselburg, West Germany.

Asexual reproduction of the new cultivar by leaf cuttings and by division of shoots, as performed by me at Isselburg, Rhineland, Germany has demonstrated that the combination of characteristics as herein disclosed for the new cultivar are firmly fixed and are retained through successive generations of asexual reproduction.

The following observations, measurements and values describe plants grown in Isselburg, Rhineland, Germany under greenhouse conditions which closely approximate those generally used in commercial practice.

The following traits have been repeatedly observed and are determined to be basic characteristics of New York which in combination distinguish this african violet as a new and distinct cultivar:

1. Intensive violet-blue flower color which doesn't fade.
2. Relatively large flower size and non-dropping flowers.
3. Excellent contrast between dark flower color and golden yellow anthers.
4. Strong and upright stems.
5. A saleable, decorative plant is available with first flash of flowering.
6. Older flower stems tend to extend toward side of bouquet to permit new stem growth in center.

7. Compact growth habit.
8. Medium green leaves.

The accompanying photographic drawings show a typical specimen plant of the new cultivar.

FIG. 1 is a perspective view of the plant and

Figure 2:
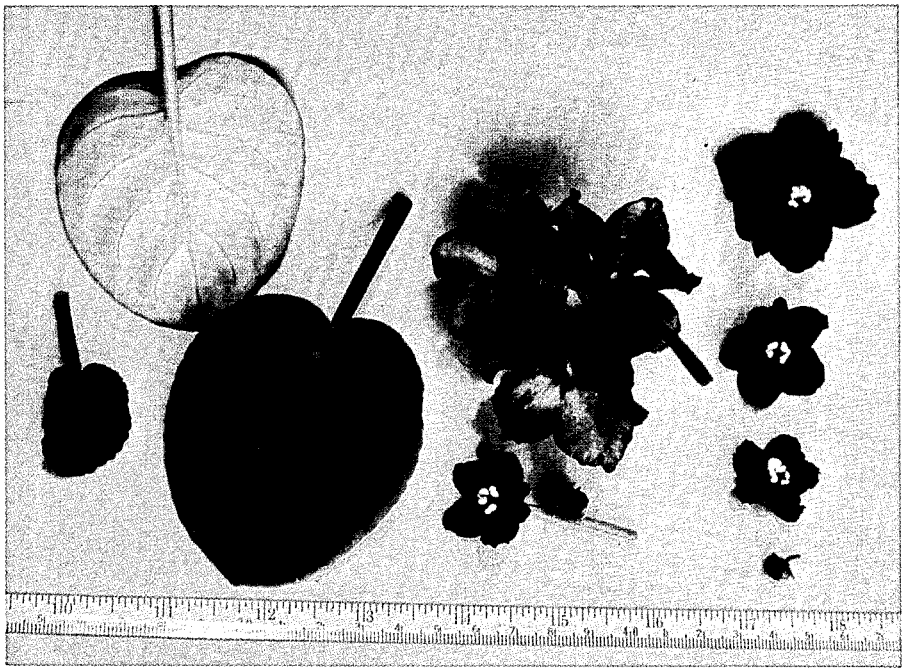

FIG. 2 comprises photographs showing various parts of the plant, top and underside, and the developing bud formations. The time from early bud formation to fully opened flowers is approximately 6–7 weeks. The colors appearing in the photographs are as true as possible with color illustrations of this type. In the following description, color references are made to the Munsell Limit Color Cascade chart, except where general color terms of ordinary significance are employed.

Botanical classification: *Saintpaulia ionantha,* Ramat. cv New York.

Parentage:

*Male parent.*—XX 224, blue, starshaped.

*Female parent.*—SL blue (color 1-13).

Propagation: The new cultivar holds its distinguishing characteristics through successive propagations by leaf cuttings and by division of shoots.

Plant:

*Size.*—From 8 cm. to 30 cm. tall when grown in pots, and approximately 20–25 cm. in diameter when fully grown.

*Leaves.*—General form: round to oval. Diameter: 6–7 cm. Texture: soft. Aspect: shiny and slightly hairy. Veins: underside well pronounced. Color: upperside, 20-15, underside, 19-2. Petiole: Green-brown.

*Flowers.*—Buds: cup-shaped, 1–3 mm. when small, 10 mm. before opening; color brown-red. Sepals: five sepals, hairy. Color: brown. Calyx: funnel-shaped. Aspect: spear-shaped. Peduncle: brown-red, strong; 1–3 cm.

*Individual flowers.*—Size: Color: Upperside — between 1-13 and 1-14. Underside — between 1-10 and 1-11. Borne: every flower stem has 4–7 flowers on short peduncles. Shape: five petals, forming star shape. Corolla: each petal on a mature flower is 20 by 20 mm. Arrangement: strong and upright. Flowering time: approximately 5–6 weeks after potting the first flowers appear, and 3 weeks thereafter the plant is in full flower.

*Reproductive organs.*—Anthers: 4-5, golden yellow; ovary, pilous. Arrangement: basifixed. Filaments: 3 mm. long, light yellow, two stripes, dark violet. Styles: base light green and hairy; upper part, violet blue. Pollen color: 26-2.

*Roots.*—Normal, well developed root system.

*Disease resistance.*—Good resistance to mildew, soft-rot and botrytis.

General observations: The intensive dark violet-blue flower color and golden yellow anthers provide a very attractive flower head. The stems are upright and strong, and the older stems tend to extend sidewards to permit new stems in the center. The plant has a long blooming period and there is only a very short time interval between blooming periods due partially to the direction of older stem movement as noted. The plant is decorative and saleable after the first flash of flowers, due primarily to flower color and size.

I claim:

1. A new and distinct cultivar of african violet known by the cultivar name New York and particularly characterized as to uniqueness by the combined characteristics of intensive violet-blue flower color which doesn't fade; relatively large flower size; strong and upright stems; compact growth habit; medium green leaves; long blooming period, and the saleability of the plant after the first flash of flowers.

* * * * *